US009533787B2

(12) United States Patent
Kwirandt

(10) Patent No.: US 9,533,787 B2
(45) Date of Patent: Jan. 3, 2017

(54) DEVICE FOR DETECTING ELEVATIONS AND/OR DEPRESSIONS ON BOTTLES, IN PARTICULAR IN A LABELING MACHINE

(75) Inventor: Rainer Kwirandt, Barbing (DE)

(73) Assignee: KRONES AG, Neutraubling (DE)

( * ) Notice: Subject to any disclaimer, the term of this patent is extended or adjusted under 35 U.S.C. 154(b) by 1042 days.

(21) Appl. No.: 12/778,226

(22) Filed: May 12, 2010

(65) Prior Publication Data

US 2010/0290695 A1 Nov. 18, 2010

(30) Foreign Application Priority Data

May 12, 2009 (DE) .................. 10 2009 020 919

(51) Int. Cl.
*H04N 7/18* (2006.01)
*B65C 9/06* (2006.01)
*G01N 21/90* (2006.01)
*G01N 21/00* (2006.01)
*G01N 21/88* (2006.01)

(52) U.S. Cl.
CPC ........... *B65C 9/067* (2013.01); *G01N 21/9036* (2013.01); *G01N 21/9045* (2013.01); *G01N 2021/8832* (2013.01)

(58) Field of Classification Search
CPC ............ G01N 21/9036; G01N 21/9045; G01N 21/909; G01N 21/9515; G01N 21/952; G01N 2033/0081; G01N 21/88; G01N 21/9018; B65C 9/067
See application file for complete search history.

(56) References Cited

U.S. PATENT DOCUMENTS

| 3,814,521 | A | * | 6/1974 | Free ........................... 356/604 |
| 4,376,951 | A | * | 3/1983 | Miyazawa ............. B07C 5/126 209/939 |
| 4,584,469 | A | * | 4/1986 | Lovalenti ................. 250/223 B |
| 4,644,151 | A | | 2/1987 | Juvinall |
| 4,691,231 | A | * | 9/1987 | Fitzmorris et al. ........... 348/127 |
| 4,697,076 | A | * | 9/1987 | Yoshida .................... 250/223 B |
| 4,750,035 | A | * | 6/1988 | Chang et al. ................ 348/127 |

(Continued)

FOREIGN PATENT DOCUMENTS

| CN | 1936496 A | 3/2007 |
| CN | 1936496 B | 5/2010 |

(Continued)

OTHER PUBLICATIONS

European Search Report for EP 10162287, dated Nov. 26, 2010.

(Continued)

*Primary Examiner* — Ryan Zeender
*Assistant Examiner* — Dana Amsdell
(74) *Attorney, Agent, or Firm* — Marshall, Gerstein & Borun LLP

(57) ABSTRACT

A device for detecting elevations and/or depressions on bottles, in particular in a labeling machine, the device comprising a lighting unit with a light screen for generating a light reflection on a bottle to be examined and at least one camera for detecting the light reflection. By areas of varying luminance being formed on the light screen, molding seams can be reliably detected over a large area of the bottle wall and embossings can be located in various rotational positions of the bottle. The invention also relates to a method for applying the device.

9 Claims, 5 Drawing Sheets

(56) References Cited

U.S. PATENT DOCUMENTS

| | | | |
|---|---|---|---|
| 4,843,231 A * | 6/1989 | Caloyannis et al. | 250/223 B |
| 4,865,447 A * | 9/1989 | Shay | G01N 21/9054 250/223 B |
| 4,868,404 A * | 9/1989 | Hajime | 250/559.22 |
| 4,915,237 A * | 4/1990 | Chang et al. | 209/524 |
| 4,948,956 A | 8/1990 | Fukuchi | |
| 5,004,909 A | 4/1991 | Fukuchi | |
| 5,059,031 A * | 10/1991 | Hamel et al. | 356/428 |
| 5,136,157 A * | 8/1992 | Apter et al. | 250/223 B |
| 5,237,404 A * | 8/1993 | Tanaka et al. | 348/128 |
| 5,278,635 A * | 1/1994 | Ono | G01N 21/952 250/559.49 |
| 5,386,293 A * | 1/1995 | Barnard et al. | 356/397 |
| 5,405,015 A * | 4/1995 | Bhatia et al. | 209/524 |
| 5,471,297 A * | 11/1995 | Tani | G01N 21/88 356/239.1 |
| 5,591,462 A * | 1/1997 | Darling et al. | 425/173 |
| 5,729,340 A * | 3/1998 | Griesbeck et al. | 356/240.1 |
| 5,889,593 A * | 3/1999 | Bareket | 356/445 |
| 6,104,482 A * | 8/2000 | Brower | G01N 21/9054 356/239.1 |
| 6,135,350 A * | 10/2000 | White et al. | 235/380 |
| 6,304,323 B1 * | 10/2001 | Ishikura | G01N 21/90 250/223 B |
| 6,320,641 B1 | 11/2001 | Bauer et al. | |
| 6,424,414 B1 * | 7/2002 | Weiland | G01N 21/90 250/223 B |
| 7,010,863 B1 * | 3/2006 | Juvinall | G01B 11/26 33/522 |
| 7,388,679 B2 | 6/2008 | Yoshino et al. | |
| 8,624,972 B2 * | 1/2014 | Kwirandt | G01N 21/9045 348/127 |
| 2002/0093812 A1 | 7/2002 | Kiest et al. | |
| 2003/0128399 A1 * | 7/2003 | Chino et al. | 358/296 |
| 2006/0037706 A1 | 2/2006 | Putzer | |
| 2008/0034628 A1 | 2/2008 | Schnuckle | |
| 2008/0037033 A1 | 2/2008 | Ersue et al. | |
| 2008/0134633 A1 | 6/2008 | Zwilling | |
| 2009/0290781 A1 * | 11/2009 | Yannick | G01N 21/8806 382/141 |
| 2010/0141756 A1 * | 6/2010 | Grote | B65C 9/067 348/127 |
| 2010/0289892 A1 | 11/2010 | Kwirandt | |

FOREIGN PATENT DOCUMENTS

| | | |
|---|---|---|
| DE | 2938235 A1 | 4/1980 |
| DE | 19519777 A1 | 12/1996 |
| DE | 68926362 T2 | 12/1996 |
| DE | 29619021 U1 | 6/1997 |
| DE | 19751399 A1 | 5/1999 |
| DE | 69510817 T2 | 11/1999 |
| DE | 10017126 C1 | 6/2001 |
| DE | 10006663 A1 | 8/2001 |
| DE | 10317078 A1 | 10/2004 |
| DE | 102004040164 A1 | 3/2006 |
| JP | 08-068767 A | 3/1996 |
| JP | 2006208053 A | 8/2006 |
| WO | WO-9817993 A2 | 4/1998 |
| WO | WO-0151887 A1 | 7/2001 |
| WO | WO-2004088295 A1 | 10/2004 |
| WO | WO-2007042673 A1 | 4/2007 |
| WO | WO-2007136248 A1 | 11/2007 |
| WO | WO-2009072157 A1 | 6/2009 |

OTHER PUBLICATIONS

Chinese Office Action for 201010178227.7 mailed Nov. 16, 2011.
German Search Report for DE 102009 020 919.0, mailed Dec. 12, 2009.
German Search Report for 10 2009 020 920.4 mailed Mar. 2, 2010.
Chinese Office Action for 201010178226.2 mailed Nov. 16, 2011.
Chinese Office Action for 201010178226.2 dated Jul. 20, 2012.
Non-Final Office Action in U.S. Appl. No. 12/770,873 dated Sep. 18, 2012.
Final Office Action in U.S. Appl. No. 12/770,873 dated Feb. 4, 2013.

* cited by examiner

DEVICE FOR DETECTING ELEVATIONS AND/OR DEPRESSIONS ON BOTTLES, IN PARTICULAR IN A LABELING MACHINE

CROSS-REFERENCE TO RELATED APPLICATION

The present application claims the benefit of priority of German Application No. 102009020919.0, filed May 12, 2009. The entire text of the priority application is incorporated herein by reference in its entirety.

FIELD OF THE DISCLOSURE

The disclosure relates to a device for detecting elevations and/or depressions on bottles as well as a method for using this device.

BACKGROUND

Elevations and/or depressions on bottle surfaces can occur e.g. at molding seams and relief-like impressions at the bottle body, the so-called embossings.

Bottles with a molding seam, such as bottles for beverages, must be preferably labeled such that the molding seam is not covered by the label. Furthermore, the label is possibly to be oriented with respect to an embossing. To detect the position of a molding seam or an embossing and permit later rotation of the bottle to a desired position, it is known to examine a lamp reflection formed on the bottle body for irregularities in various rotational positions of the bottle. In the process, normally only a portion of the molding seam or the embossing, respectively, can be detected by the lamp reflection.

DE 10 2004 040 164 A1, for example, describes a semicircular, uniformly illuminated lamp shade arranged coaxially around the axis of symmetry of a bottle to be examined and comprising an aperture through which the surface of the bottle is examined for irregular reflections by means of a camera. In case of profiled bottle surfaces, however, the edges of the light reflections can have an irregular shape and be difficult to detect exactly in a low-contrast representation. Furthermore, the molding seam might only be represented in a small area at the edge of the light reflection. With the known technique, the molding seam is therefore not always reliably detected.

Embossings are preferably arranged in the area of the shoulder of the bottle. In the usual horizontal viewing direction of the camera, the embossing is then often located outside of the lamp reflection. Therefore, comparably low-contrast, irregular reflections are formed at the embossing the shape of which changes while the bottle is rotated.

Due to these problems, a check measurement with an additional fine adjustment of the bottle is required. This requires an additional inspection device and much space in the labeling machine which is not desired.

SUMMARY OF THE DISCLOSURE

It is therefore an aspect of the disclosure to reliably detect molding seams over a maximum area of the bottle wall and to locate embossings in various rotational positions of the bottle as reliably as possible.

This is achieved by areas of varying luminance being formed on the light screen of the lighting unit. These superimpose the structures to be detected in the reflection and cause reflection zones of varying brightness, in particular with bright lines on a dark background and dark lines on a bright background. This facilitates the detection of molding seams and embossings.

Preferably, the areas of varying luminance are arranged in a stripe pattern. Thereby, a regular pattern enhancing the image contrast is provided in the reflection.

In one embodiment, the stripe pattern comprises two to four dark stripes. This improves the representation in essentially cylindrical bottle shapes which image vertical structures with a sharper definition and more compactly than horizontal structures.

Preferably, the areas of varying luminance alternate in the horizontal direction. This improves the detection of vertically running molding seams which mainly cause reflection disturbances in the horizontal direction.

Preferably, the transition of the luminance between the areas of varying luminance is gradual. This supports the evaluation of the camera images filtered with band-pass filters.

In one preferred embodiment, the areas of varying luminance are embodied as areas of varying light transmissions. Thereby, dark screen areas can be easily realized.

Preferably, the light screen comprises a foil on or in which the areas of varying luminance are formed. This permits an inexpensive and flexible realization of areas of varying luminance, e.g. by printing the foil, as well as an easy change between various illumination patterns.

In one preferred embodiment, the lighting unit furthermore comprises a light source and the light screen furthermore comprises a diffusion screen, the foil being disposed between the light source and the diffusion screen. In this manner, undesired print artifacts of the foil can be smoothened, such as e.g. superimposed patterns and stripes.

Preferably, the light screen has the shape of a funnel opened towards the bottle. In this manner, a sheet-like expanded reflection can be generated on the cylindrical bottle section as well as on the shoulder of the bottle.

In one preferred embodiment, the camera is inclined towards the bottom of the bottle, its optical axis including an angle of maximally 80° with the main axis of the bottle. Thus, not only large areas of the molding seam can be imaged, but the lamp reflection also permits a particularly advantageous representation of the shoulder region of the bottle.

Preferably, the device further comprises a transport means for the bottle for passing through an image recording region of the camera and a rotating support arranged on the transport means for retaining the bottle. With these, a continuous stream of bottles in various rotational positions can be inspected.

Another embodiment comprises a calculation unit for evaluating the detected reflection, for locating the elevations and/or depressions and for determining an actual rotational position of the bottle. Thereby, the bottle can be subsequently moved to a desired rotational position.

The one aspect of the invention is moreover achieved by a method for applying the device according to the disclosure, wherein the bottle is illuminated with the light screen, so that the light reflection at least temporarily overlaps the elevations and/or depressions to be detected, and the reflection is imaged with a camera. The superimposition of the structures to be detected with the areas of varying brightness of the light screen causes reflection zones of varying brightness, in particular bright lines on a dark background and dark lines on a bright background. This facilitates the detection of molding seams and embossings.

Preferably, the bottle is in the process moved through an image-recording area of the camera while it is rotated about its longitudinal axis, so that the reflection is imaged in various rotational positions of the bottle. Thereby, a continuous stream of bottles in various rotational positions can be inspected.

In one preferred embodiment, a calculation unit evaluates the camera images, detects the position of the elevations and/or depressions and determines from these an actual rotational position of the bottle. Thereby, the bottles can be subsequently moved to a desired rotational position.

BRIEF DESCRIPTION OF THE DRAWINGS

Preferred embodiments are represented in the drawing and will be illustrated below. In the drawings.

DETAILED DESCRIPTION OF THE PREFERRED EMBODIMENT

Figure 1:
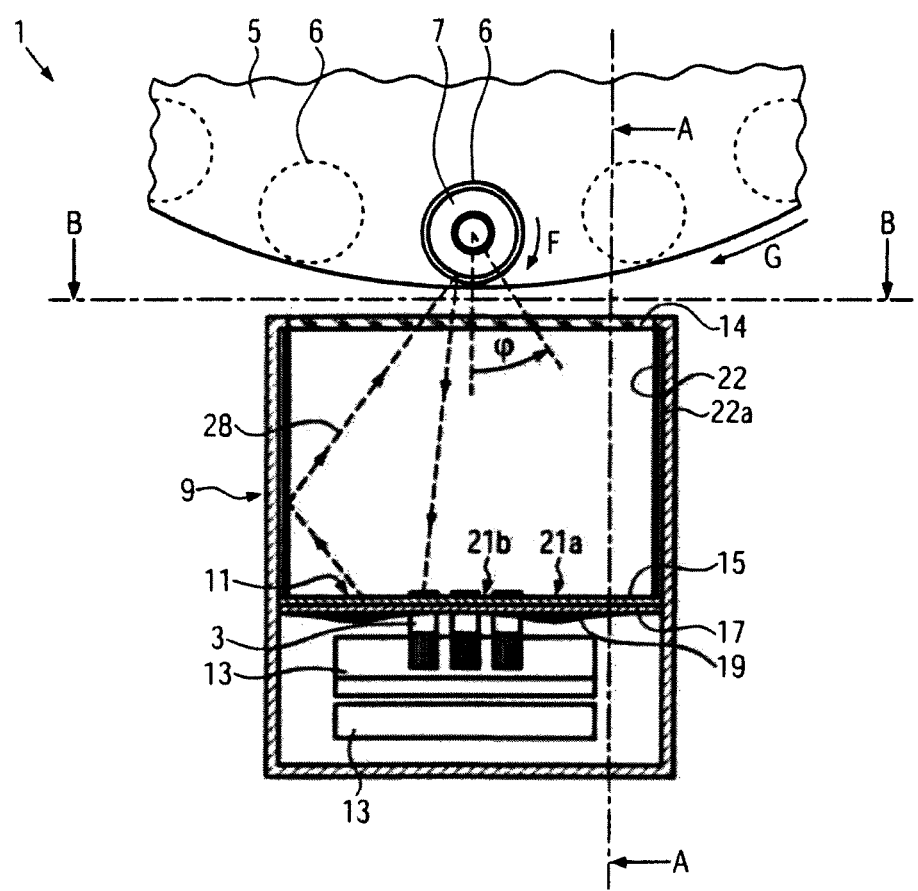
FIG. 1 shows a schematic plan view onto a first embodiment, seen through the cutting plane C-C of FIG. 2.
Figure 2:
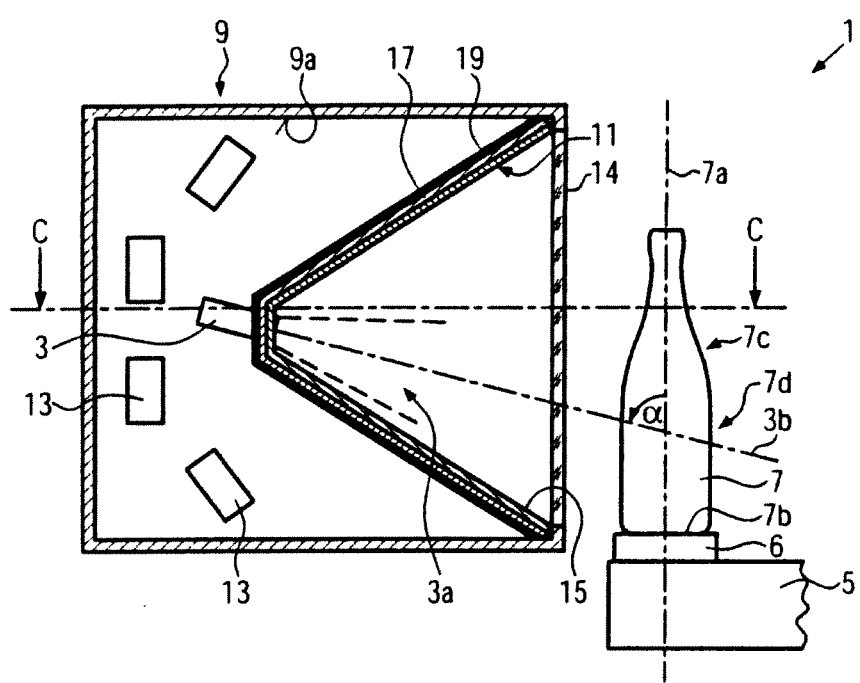
FIG. 2 shows a schematic side view of the first embodiment, seen through the cutting plane A-A of FIG. 1.

As can be seen in FIGS. 1 and 2, the inspection device 1 according to the disclosure comprises three cameras 3, each having an image area 3a indicated by a dashed line, for imaging a bottle 7 passing the cameras 3 on a rotating transport means 5 (see arrow G). The cameras 3 are integrated in a lighting unit 9 with a funnel-shaped light screen 11, several lamps 13 and a safety screen 14. The bottle 7 is held upright and centered with respect to the main axis 7a of the bottle 7 by a rotating support 6, such as a motor-driven rotary table with a lowerable centering device. Supports 6 for further bottles 7 for examining a continuous stream of bottles are indicated in a dotted line. The drive of the supports 6 is not represented and is symbolized by arrow F.

Figure 3:
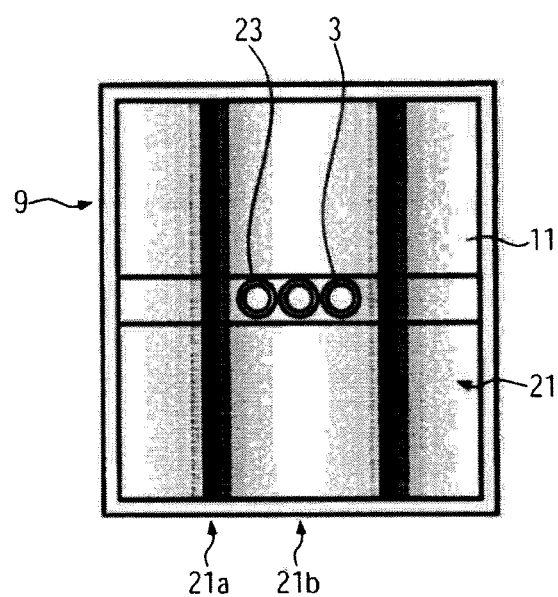
FIG. 3 shows a schematic front view of the first embodiment, seen through the cutting plane B-B of FIG. 1.

The light screen 11 comprises a diffusion screen 15, such as an opal glass screen or a translucent plastic screen, on its side facing the bottle 7, and a foil 17 printed with a colorant 19 in sections of varying intensities on its side facing the lamps 13. The layer thickness of the colorant 19 is represented in the figures in a highly exaggerated way for a better understanding, where areas of a great layer thickness correspond to areas of low luminance and vice-versa. The light transmission of the colorant 19 repeatedly varies in the horizontal direction along the light screen 11, so that on the light screen 11, dark areas 21a with a low level of luminance alternate with bright areas 21b with a high level of luminance in the horizontal direction. The transition of the luminance from the dark areas 21a to the bright areas 21b and vice-versa is gradual. It becomes clear in particular from the parallel perspective of FIG. 3 that the areas 21a,b of varying luminance form an essentially vertically oriented stripe pattern 21 on the light screen 11.

As can be further seen in FIG. 1, the lighting unit 9 comprises lateral mirrors 22 which are preferably embodied as mirror foils attached to a transparent mirror body 22a. These reflect light 28 emitted from the light screen 11 towards the bottle 7.

According to FIG. 2, the cameras 3 are inclined towards the bottom of the bottle 7b, its optical axis 3b including an angle α of maximally 80° with the main axis 7a of the bottle. Here, the camera 3 views through a camera port 23 in the light screen 11 diagonally downwards onto the transitional area of the shoulder of the bottle 7c with the cylindrical section 7d of the bottle 7. Thus, with the camera 3, one obtains the camera image 25 with the light reflection 27 schematically represented in FIG. 4, which is a reflected image of the light screen 11 distorted by the bottle 7. The dark or bright stripes 27a,b of the light reflection 27 here essentially correspond to the areas 21a,b of the stripe pattern 21.

The reflection 27 contains additional dark and bright stripes 27a' and 27b', respectively, which correspond to the areas 21a,b reflected at the mirrors 22. This proportion of the reflection 27 reflected at the mirrors 22 is schematically indicated by the ray of light 28 in FIG. 1. The number of reflected stripes 27a' and 27b' in the reflection 27 depends on the dimensioning of the lighting unit 9 and the distance between the light screen 11 and the bottle 7. If this distance would be successively increased in the example, the lateral edges of the reflection 27 would migrate inwards, and first the outer stripes 27b', then the adjacent stripes 27a' would be "cut out" of the reflection 27.

Figure 4:
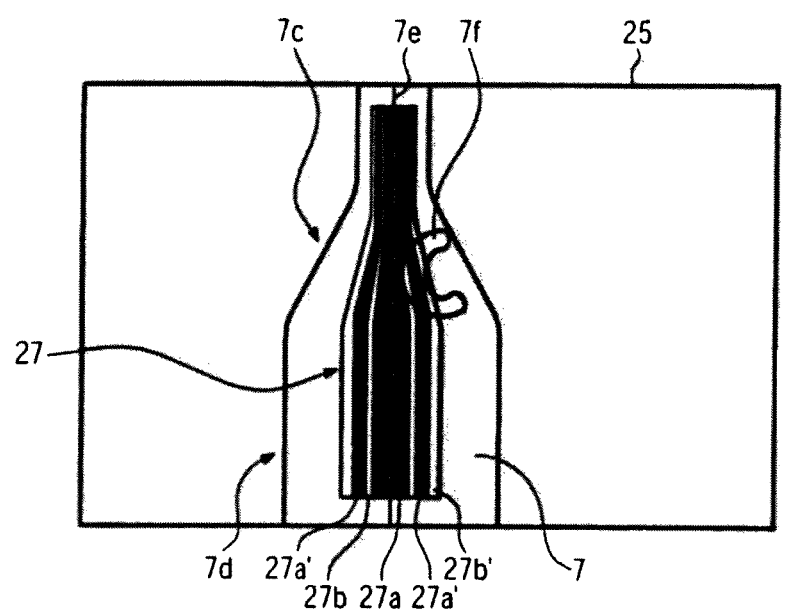
FIG. 4 shows a schematic representation of a camera image with a light reflection for detecting elevations or depressions, respectively, on a bottle to be examined.

In FIG. 4, a molding seam 7e and an embossing 7f are moreover shown which are embodied like a relief and/or as a depression on the bottle 7. Camera images 25 taken in various rotational positions φ, e.g. at distances of 30° each, are evaluated in a (non-depicted) calculation unit 29 to locate the molding seam 7e and/or the embossing 7f, and in this manner determine an actual rotational position $\phi_I$ of the bottle 7. Normally, the bottle surface 7c, 7d is completely laid out in front of the cameras 3 for doing so.

In the camera image 25, the contours of the molding seam 7e and the embossing 7f appear sharply defined, e.g. as bright lines on the dark stripes 27a,a' or as dark lines on the bright stripes 27b,b'. In contrast, the transitions between the stripes 27a,a',b,b' are gradual like the transitions between the areas 21a,b of the stripe pattern 21. This supports band-pass filtering in the evaluation of the camera image 25 for distinguishing between the contours of the molding seam 7e or the embossing 7f and the stripes 27a,a',b,b'. The stripes 27a,a',b,b' of the reflection 27 are perspectively distorted with respect to the areas 21a,b of the light screen and appear to be compressed due to the essentially cylindrical shape of the bottle 7 in the horizontal direction.

The number of dark stripes 27a,a' in the reflection 27 is preferably three to eight. Thereby, the molding seams 7c and embossings 7d can be equally well detected. Depending on the number of dark areas 21a reflected at the mirrors 22 and utilizable in the reflection 27, the number of the areas 21a of the light screen 11 is preferably one to eight, in a particularly advantageous further development of the disclosure two to four. However, the device is not restricted to the respective above mentioned number of dark stripes 27a,a' or 21a.

To be able to detect the molding seam 7e as reliably as possible, the stripes 27a,a',b,b' are oriented essentially in parallel to the molding seam 7e. However, it is also possible to orient the stripes 27a,a',b,b' diagonally with respect to the molding seam 7e, e.g. at an angle of up to 10°. This improves the molding seam detection in the center of the camera image 25. In such a case, the areas 21a,b must be correspondingly disposed obliquely on the light screen 11, e.g. at angles of up to 10° with respect to the vertical.

An "essentially vertically oriented" stripe pattern 21 means that on an upright bottle 7, the stripe pattern 21 generates a reflection 27 with stripes 27a,a',b,b' oriented essentially in parallel to the molding seam 7e or the main axis 7a of the bottle 7. In a deviating examination position, the orientation of the stripe pattern 21 on the light screen 11 would have to be adapted correspondingly.

In general, it is possible to provide other brightness distributions on the light screen 11, e.g. essentially horizontally oriented stripe patterns or ring patterns, to be able to particularly reliably detect specially shaped elevations and/or depressions on the bottle 7.

The cameras 3 are inclined such that not only large areas of the molding seam 7e can be observed in a camera image 25. Moreover, the reflection 27 is then particularly suited for detecting embossings 7f in the shoulder area 7c of the bottle. Depending on the bottle shape, the angle α can be, for example, 30 to 80, but also 80 to 90, if required. The reflection 27 preferably completely includes the embossing 7f in the vertical direction, so that it can be reliably detected in various rotational positions of the bottle 7.

For an uncomplicated adjustment of the inspection device 1 to different bottle types and/or structures 7e,f to be detected, in particular for the height adjustment of the reflection 27, the lighting unit 9 is preferably embodied to be height adjustable.

The device 1 according to the disclosure can be equipped with several cameras 3, of which the image-recording areas 3a overlap laterally, so that the bottle 7 passing the cameras 3 is imaged in various, predetermined rotational positions φ across its complete periphery while it is simultaneously rotated on the support 6. The number of cameras 3 is not restricted to the shown example. Preferably, the distance between the cameras 3 is minimal to ensure as standardized imaging conditions as possible.

The light screen 11 is funnel-shaped and its surface is as large as possible to receive a reflection 27 as large as possible which smoothly passes from the cylindrical part 7d of the bottle 7 to the shoulder of the bottle 7. Thereby, the number of camera images 25 required for a reliable inspection of the bottle 7 can be minimized.

The light screen 11 and the foil 17 consist of several, preferably flat segments. This permits an easy integration of the printed foils 17 into the light screen 11. However, the light screen 11 could also be formed in one piece and/or comprise curved surfaces, such as ellipsoid segments.

The gradual transition of the luminance from the areas 21a to the areas 21b and vice-versa preferably corresponds to a waved pattern, for example a sinusoid.

The colorant 19 can be printed on any side of the foil 17, or else on both sides of the foil 17. It is also possible to incorporate the colorant into the foil 17. It is also conceivable to apply the colorant 19 directly onto the side of the diffusion screen 15 facing the lamp 13. The use of a foil 17, however, is advantageous in that one can easily change between various stripe patterns 21 to adapt the device to certain bottle shapes and/or structures on the bottle surface.

Advantageously, the colorant 19 primarily has an optical absorption effect to form the areas 21a with a low level of luminance. However, it would also be possible to form the areas 21b with a high level of luminance by means of a fluorescent colorant 19. The areas 21a,b could also be formed by a combination of absorbing and/or fluorescent colorants 19.

The light sources 13 are e.g. LED background lamps. However, other types of lamps can also be used. The arrangement of the light sources 13 is not restricted to the example in FIGS. 1 and 2. It is also possible to only use one light source 13 in the lighting unit 9.

As an alternative, the dark and bright areas 21a,b could be generated by an illumination of the light screen 11 of varying brightness in sections. To this end, the light sources 13 could be embodied as LED matrix of which the LED elements emit light at different levels of brightness. Depending on the number and size of the elements, these would have to be arranged at a suited distance to the diffusion screen 15, so that a smoothed illumination pattern 21 with gradual brightness transitions is formed. With this variant, different patterns 21 could also be generated without any modifications.

The lighting unit 9 preferably comprises reflecting or highly backscattering inner walls 9a, such as they are known, for example, from Ulbricht spheres, to increase light efficiency and/or ensure a uniform illumination of the light screen 11.

This improves the quality of the camera images with short exposure times. For this purpose, the lighting unit can also be provided with additional mirrors and/or backscattering dividing walls (not shown). The screen 14 protects the lighting unit 9 from soiling, however, it is not imperative.

The transparent mirror body 22a, in particular in cooperation with reflecting or backscattering inner walls 9a, causes the light screen 11 to be illuminated from different directions, and thus with an optimally uniform brightness, even in the transitional area to the mirrors 22. Thereby, dark, sharply defined lines are avoided at the transition from the light screen 11 to the mirror 22 and in the corresponding areas of the reflection 27, respectively.

The transport means 5 is preferably a transport carousel as indicated in FIGS. 1 and 2. However, it could also be linear or curved. The senses of rotation F and G of the support 6 and of the transport means 5 are preferably identical, but they could also be contradirectional.

Hereinafter, a second embodiment will be described which essentially differs from the first embodiment by an alternative funnel shape of the light screen 11 and by no lateral mirrors 22 being provided. If nothing to the contrary is stated, the other features correspond to those of the first embodiment and are therefore not described again, and some of them are not provided with reference numerals in FIGS. 5 and 6.

Figure 5:
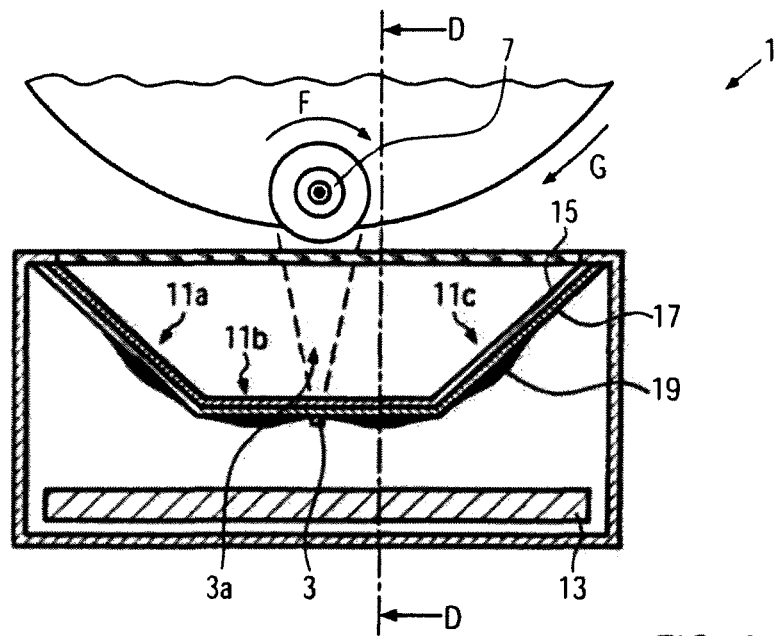
FIG. 5 shows a schematic plan view onto a second embodiment, seen through the cutting plane E-E of FIG. 6.
Figure 6:
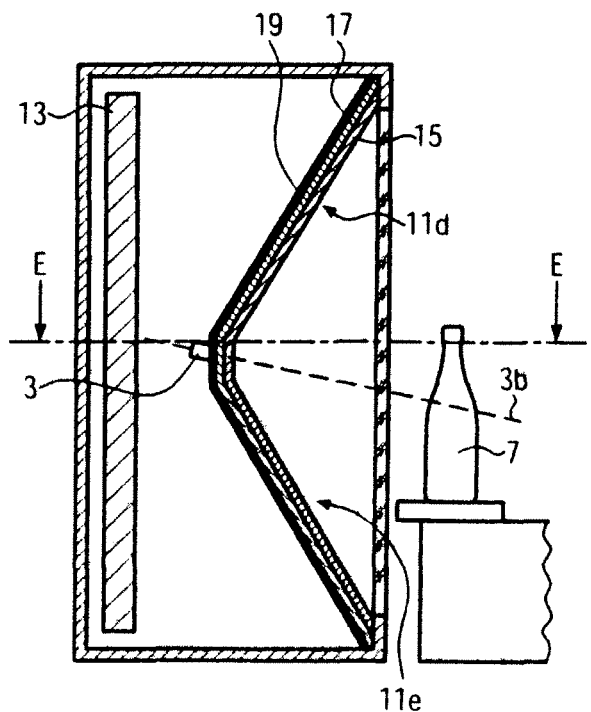
FIG. 6 shows a schematic side view of the second embodiment, seen through the cutting plane D-D of FIG. 5.

As one can see in FIG. 5, the light screen 11 of the second embodiment has a funnel shape also in the plan view. It can be formed, for example, of five flat segments 11a-e which each face an examination position of the bottle 7 within the image-recording area 3a. In the second embodiment, the areas 21a,b are not only embodied on the central segments 11b,d,e, but also on the lateral segments 11a,c. Therefore, the reflection 27 shown in FIG. 4 also results when the bottle 7 is irradiated, wherein, however, the stripes 27a',b' of the first embodiment generated by reflection at the mirrors 22 are replaced in the second embodiment by further stripes 27a,b generated by means of direct irradiation of the bottle 7. Correspondingly, the preferred number of dark areas 21a of the light screen 11 is three to eight in the second embodiment.

The dark and bright areas 21a,b can be inclined to varying degrees with respect to the vertical, depending on the design of the light screen 11, so that essentially vertically oriented stripes 27a,b result in the reflection 27. In the front view, the stripes 21a and/or 21b preferably include an angle of maximally 45° with the vertical or the main axis 7a of the bottle 7 in the parallel perspective. Suited stripe patterns 21 can be calculated e.g. by ray tracing for a predetermined funnel shape, so that a predetermined reflection 27 results on the bottle type to be examined in the simulation.

The features of the described embodiments can be combined. In particular, the design of the light screen 11 is not restricted to the shown examples. For example, the screens could be tilted orthogonally, so that their plan view becomes the side view and vice-versa. Equally, the areas 21a,b could be embodied on (non-depicted) bent sections of the light screen 11.

One can work as follows with the inspection device according to the disclosure:

A bottle 7 fixed to the support 6 is moved along the transport path 5 into the recording area 3a of a camera 3, while it is simultaneously rotated about its longitudinal axis 7a. As long as the bottle 7 is within the image area 3a of the camera 3, recordings 25 of the reflection 27 are taken in predetermined rotational positions $\phi$ of the bottle 7 or at predetermined intervals, respectively, and these recordings are further processed with an image evaluation in the calculation unit 29. When the bottle 7 leaves the image area 3a of the camera 3 before the total periphery of the bottle 7 could be examined (depending on the transport or rotational speed of the transport means 5 or the support 6, respectively), the image area 3a is followed by at least one further image area 3a of a further camera 3 so as to overlap until the total bottle periphery has been detected by the camera recordings 25. By evaluating the recordings 25 in the calculation unit 29, the position of a molding seam 7e and/or an embossing 7f is detected and an actual rotational position $\phi_I$ of the bottle 7 or the support 6 is determined, so that subsequently the bottle 7 can be moved to a desired rotational position $\phi_S$.

The invention claimed is:

1. An inspection device for detecting elevations and/or depressions on bottles, in particular in a labeling machine, comprising:
    a lighting unit with a light screen for generating a light reflection on a bottle to be examined;
    at least one camera for imaging the bottle and the light reflection, the bottle specularly reflecting the light from the light screen so that the light reflection from the bottle constitutes a distorted image of the light screen;
    a transport means moving the bottle through an image-recording area of the camera; and
    a rotating support arranged on the transport means for fixing the bottle on the support and for rotating the bottle into predetermined rotational positions;
    the light screen comprising areas of varying brightness, and being embodied as one or more of:
        at least one light source and a diffusion screen having areas of varying light transmission,
        at least one light source and foil having areas of varying light transmission, and
        a matrix of light sources emitting light at different levels of brightness,
    wherein the transition between the areas of varying brightness across the light screen is a gradual transition corresponding to a waved pattern, the areas of varying brightness alternating in a horizontal direction with respect to the bottle.

2. The inspection device according to claim 1, wherein the areas of varying brightness are arranged in a stripe pattern.

3. The inspection device according to claim 2, characterized in that the stripe pattern comprises two to four dark stripes.

4. The inspection device according to claim 1, wherein the light screen comprises at least one foil in and/or on which the areas of varying brightness are formed.

5. The inspection device according to claim 4, wherein the lighting unit comprises at least one light source, the light screen further comprises a diffusion screen, and the foil is arranged between the light source and the diffusion screen.

6. The inspection device according to claim 1, wherein the light screen has the shape of a funnel opened towards the bottle.

7. The inspection device according to claim 1, wherein the camera is inclined towards the bottom of the bottle and its optical axis includes an angle (a) of maximally 80° with the main axis of the bottle.

8. The inspection device according to claim 1, further comprising:
    a calculation unit for evaluating the detected reflection, for locating the elevations and/or depressions, and for determining an actual rotational position ($\phi_I$) of the bottle.

9. The inspection device of claim 1, wherein at least one camera captures an image of the bottle to be examined and the light reflection, and
    wherein the transition between the areas of varying brightness across the light screen causes the light reflection to have areas of gradual transitions of brightness in the horizontal direction to facilitate band pass filtering as the image is evaluated.

* * * * *